United States Patent [19] [11] 3,942,973
Wittenbrook et al. [45] Mar. 9, 1976

[54] HERBICIDAL COMPOSITIONS CONTAINING PARA-SUBSTITUTED BENZENESULFONYLUREAS AND SALTS THEREOF AND METHODS OF EMPLOYING SUCH COMPOSITIONS

[75] Inventors: Lawrence S. Wittenbrook, Doylestown, Pa.; Richard J. Timmons; Raymond D. Fleming, both of Marysville, Ohio

[73] Assignee: The O. M. Scott & Sons Company, Marysville, Ohio

[22] Filed: May 13, 1974

[21] Appl. No.: 469,525

Related U.S. Application Data

[60] Division of Ser. No. 323,372, Jan. 15, 1973, abandoned, which is a continuation-in-part of Ser. No. 157,712, June 28, 1971, abandoned.

[52] U.S. Cl. ............ 71/103; 260/397.7 D; 424/321
[51] Int. Cl.² ........................................... A01N 9/14
[58] Field of Search ...................................... 71/103

[56] References Cited
UNITED STATES PATENTS

| | | | |
|---|---|---|---|
| 3,498,780 | 3/1970 | Soper et al. | 71/103 |
| 3,628,946 | 12/1971 | Tung et al. | 71/103 |
| 3,637,366 | 1/1972 | Wietelmann et al. | 71/103 |

FOREIGN PATENTS OR APPLICATIONS

| | | | |
|---|---|---|---|
| 3,918,852 | 3/1964 | Japan | 71/103 |
| 429,276 | 10/1967 | Japan | 71/103 |

OTHER PUBLICATIONS
Blank et al., "The Synthesis of Some Potential etc;" (1960).
J. Org. Chem. 26 pp. 1551–1553 (1961).

*Primary Examiner*—Glennon H. Hollrah
*Attorney, Agent, or Firm*—Strauch, Nolan, Neale, Nies & Kurz

[57] ABSTRACT

Benzenesulfonylureas of the formula:

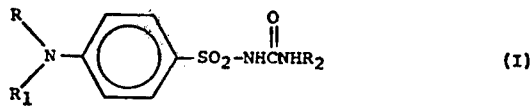

(I)

where R is methyl or ethyl, $R_1$ is methyl or ethyl, and $R_2$ is hydrogen, methyl, or ethyl and salts of those benzenesulfonylureas of formula I having the formula:

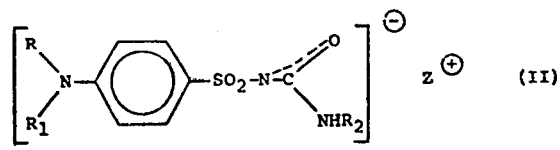

(II)

where R, $R_1$, and $R_2$ are as aforesaid, and Z is an alkali metal, an alkaline earth metal, or

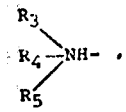

where $R_3$, $R_4$, and $R_5$ are each hydrogen or a $C_1$–$C_4$ alkyl; the use of compounds of formulas I and II; and compositions containing such compounds.

10 Claims, No Drawings

HERBICIDAL COMPOSITIONS CONTAINING PARA-SUBSTITUTED BENZENESULFONYLUREAS AND SALTS THEREOF AND METHODS OF EMPLOYING SUCH COMPOSITIONS

This is a division of application Ser. No. 323,372, filed Jan. 15, 1973 now abandoned which application is a continuation-in-part of application Ser. No. 157,712 filed June 28, 1971, for PARA-SUBSTITUTED BENZENESULFONYLUREAS, now abandoned.

The present invention relates to one aspect to chemical compounds and, more particularly, to certain novel parasubstituted benzenesulfonylureas and their salts. In another aspect, the invention relates to the use of such compounds, especially as post-emergent, selective herbicides.

The novel benzenesulfonylureas we have invented are represented by the general structural formula:

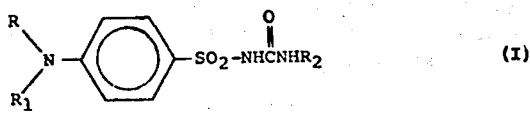

where R is methyl or ethyl, $R_1$ is methyl or ethyl, and $R_2$ is hydrogen, methyl, or ethyl.

Those salts which we have invented are represented by the formula:

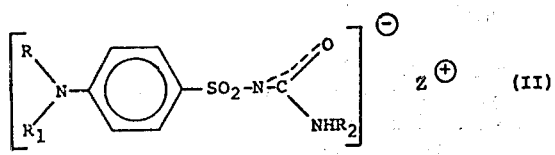

where R, $R_1$, and $R_2$ are as aforesaid, and Z is an alkali metal, an alkaline earth metal, or

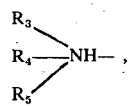

where $R_3$, $R_4$, and $R_5$ are each hydrogen or a $C_1$–$C_4$ alkyl.

The compounds of formulas I and II are particularly useful as selective, post-emergence controls for crabgrass (*Digitaria spp.*) in Southern grasses such as Zoysia, centipedegrass, bermudagrass, St. Augustinegrass, and bahiagrass.

Because of the similarities in genetic make-up, it is extremely difficult to control weedy grasses in a lawn or other turf area without damaging desirable grasses existent in the area to an unacceptable extent. This is particularly true when the weed is a crabgrass and the desirable grass is one of the Southern grasses. Accordingly, the invention of the novel benzenesulfonylureas and salts identified above and the discovery that they exhibit good selectivity between crabgrasses and Southern grasses as well as a high degree of activity against crabgrasses is an important advance in the field of turf management.

In addition to selective post-emergence activity, compounds of the present invention possess pre-emergence herbicidal activity; and at least one of them has additional types of biocidal activity. And other uses of these compounds may still remain to be discovered. Accordingly, while our invention resides in one aspect in the use of the compounds, it is to be understood that the invention in toto is of broader scope and includes the compounds as such irrespective of the uses to which they may be put as well as certain novel formulations in which they may be incorporated.

The objects of the invention include the proovision of:

1. novel sulfonylureas of formula I and those salts thereof of formula II.
2. novel, improved methods of selectively controlling the growth of monocotyledon pests in turfgrasses.
3. novel, improved herbicidal formulations which include compounds of formulas I and II.

A further important but more specific object of the invention resides in the provision of novel, improved methods for selectively controlling the growth of crabgrass in Southern grasses.

Other important objects and features as well as additional advantages of the invention will become apparent from the appended claims and from the ensuing detailed description and discussion of the invention.

The sulfonylureas of the present invention (i.e., the compounds of formula I) are prepared by procedures paralleling that described for the preparation of 1-(4'-dimethylaminobenzenesulfonyl)-3-n-butylurea in Blank et al., *The Synthesis of Some Potential Hypoglycemic Agents*, J. Org. Chem., 26, 1551 (1961). The general procedure we follow is:

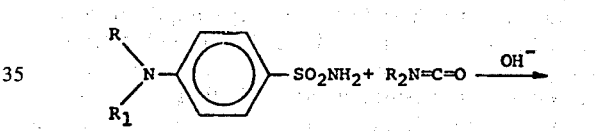

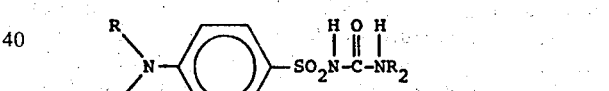

The following examples are illustrative of the application of the general procedure described above to the production of different ones of the compounds of formula I we have invented.

EXAMPLE I

The preparation of 1-(4'-dimethylaminobenzenesulfonyl)-3-ethylurea,

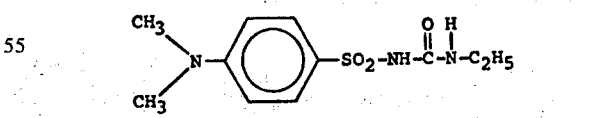

is illustrative of the procedure for preparing the 3-substituted sulfonylureas of our invention. This compound was made by combining p-dimethylaminobenzenesulfonamide[1] (45.0 g, 0.23 mole), sodium hydroxide (9.2 g, 0.23 mole), 240 ml water, and 300 ml acetone in a reaction vessel. The solution was cooled to 10°C.; and ethyl isocyanate (17.8 g, 0.25 mole) was added dropwise over a period of one hour. The reaction mixture was then refluxed for 2 hours. Reduction of the volume of solvent to 200 ml in vacuo and dilution with 700 ml water precipitated a solid which was removed by filtration. The pH of the filtrate was reduced to 3 with concentrated hydrochloric acid. This also gave a precipitate. When dried the precipitate weighed 15.7 g. It was identified as 1-(4'-dimethylaminobenzenesulfonyl)-3-ethylurea, melting point 190°–210°C.

[1.] A procedure for making p-dimethylaminobenzenesulfonamide,

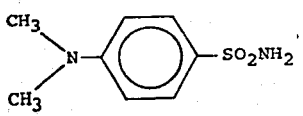

is described in Kumler, *The Absorption Spectra of Some Para Substituted Aniline Derivatives. The Presence of x' Bands*, J. Am. Chem. Soc., 68, 1184 (1946).

EXAMPLE II

The procedure by which we prepare p-diethylaminobenzenesulfonylurea.

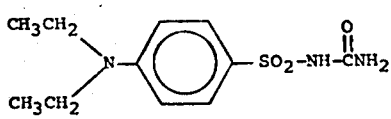

typifies that which we follow in preparing the unsubstituted formula I compounds of the present invention. This compound was made by combining p-diethylaminobenzenesulfonamide[2] (22.9 g, 0.09 mole) and potassium cyanate (11.7 g, 0.15 mole) with 125 ml ethanol and 20 ml water in a reaction vessel. The mixture was refluxed for 3 hours. Evaporation in vacuo of the reaction mixture produced a residue which was stirred with 600 ml water. Removal of this insoluble solid by filtration and acidification of the resulting filtrate to a pH of 3 with concentrated hydrochloric acid gave a precipitate. When dried, this yielded 10.9 g of p-diethylaminobenzenesulfonylurea, melting point 190°–210°C.

The formula I compounds of our invention with unsymmetrical para-amino substituents can be prepared from the corresponding sulfonamides in the same manner as those with symmetrical substituents. The starting compounds can be prepared by following

[2.] A method of preparing p-diethylaminobenzenesulfonamide is described in Kumler, supra. the method of Kumler with the substituents being added stepwise to the amino nitrogen. That is,

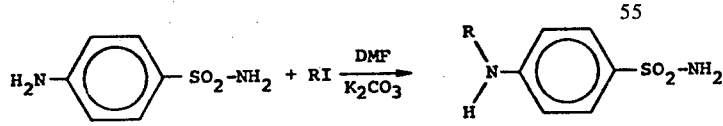

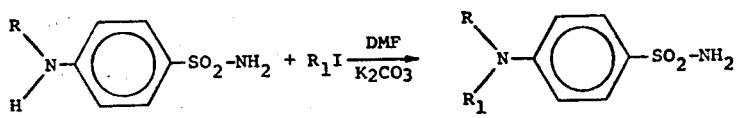

The following table gives the chemical analyses for various sulfonylureas of formula I prepared in accord with the procedure first described above in Example II:

TABLE I

| Compound | Calculated | Found | Melting Points °C. (uncorrected) |
|---|---|---|---|
| p-dimethylaminobenzenesulfonylurea | C, 44.43<br>H, 5.39<br>N, 17.27 | C, 44.05<br>H, 4.95<br>N, 16.76 | 225–228 |
| 1-(4'-dimethylaminobenzenesulfonyl)-3-methylurea | C, 46.68<br>H, 5.88<br>N, 16.33<br>S, 12.46 | C, 44.60<br>H, —<br>N, 16.32<br>S, 11.39 | 207–209 |
| 1-(4'-dimethylaminobenzenesulfonyl)-3-ethylurea | C, 49.24<br>H, 5.25<br>S, 11.95 | C, 48.42<br>H, 6.40<br>S, 11.63 | 181–183 |
| p-diethylaminobenzenesulfonylurea | C, 48.69<br>H, 6.31<br>N, 15.49 | C, 48.42<br>H, 6.64<br>N, 14.70 | 190–210 |
| 1-(4'-diethylaminobenzenesulfonyl)-3-ethylurea | C, 52.15<br>H, 7.07<br>N, 14.04<br>S, 10.71 | C, 52.35<br>H, —<br>N, 13.88<br>S, 10.82 | 192–194 |

The compounds of the present invention of formula II are prepared by reacting the parent formula I compound with an appropriate base. The preparation of representative formula II compounds is described in the following examples:

EXAMPLE III

Preparation of n-Butylamine Salt of $N^4,N^4$-Dimethylsulfanilylurea,

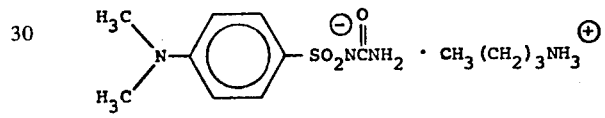

To a stirred, refluxing slurry of $N^4,N^4$-dimethylsulfanilylurea (14.6 g, 60 m moles) in acetone was added dropwise n-butylamine (5.1 g, 70 m moles) dissolved in acetone. The reaction mixture was refluxed for a total of 1.5 hours and then stirred overnight at ambient temperature.

An insoluble white solid formed. This was removed by filtration and dried, giving 3.5 g. (30 m moles) of the salt identified above. Recrystallization of this material from ethanolwater gave the pure salt in the form of white needles with a melting point of 156°–158°C.

EXAMPLE IV

Preparation of Calcium Salt of $N^4,N^4$-Dimethylsulfanilylurea,

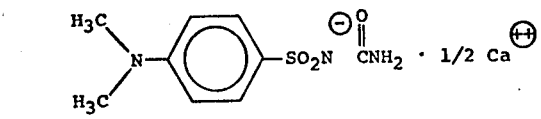

First, the sodium salt of the above-identified urea was prepared in solution by adding $N^4,N^4$-dimethylsulfanilylurea (14.6 g, 60 m moles) to a solution of sodium hydroxide (2.4 g, 60 m moles) dissolved in 200 ml water. The solution was warmed slightly to effect dissolution and reaction of the urea with base.

To this solution was added calcium chloride dihydrate (5.1 g, 35 m moles) in 50 ml water. A white precipitate formed during the addition of the calcium chloride solution.

The reaction mixture was diluted with 400 ml water and stirred overnight at ambient temperature. After filtration and drying of the white precipitate, there remained 13.1 g (50 m moles) of the calcium salt, which had a melting point >300°C.

EXAMPLE V

Preparation of Ammonium Salt of $N^4,N^4$-Dimethylsulfanilylurea,

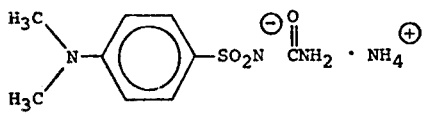

$N^4,N^4$-dimethylsulfanilylurea (4.9 g, 20 m moles) was added to an ethanol-water solution consisting of 150 ml ethanol and 75 ml water. A fourfold molar excess of an aqueous ammonium hydroxide solution (30% ammonia) was added to the above, and the resulting reaction mixture was stirred for two hours at 35°C.

Removal of the white, insoluble portion which formed by filtration left an ethanol-water filtrate which was treated with anhydrous ether. The ether soluble portion was separated from the water layer by decanting, and the water layer was diluted with 400 ml of acetone, precipitating a white solid.

The white solid was removed by filtration, washed with several portions of ether and dried, giving 2.0 g (8 m moles) of the ammonium salt, which had a melting point of 196°–210°C.

Other of the compounds of formula II can be made by procedures comparable to those described in Examples III–V.

In most cases the compounds of formula II we have prepared can be identified as the desired compounds by conventional analytical techniques. In some instances, however, the compounds hydrate readily, making analytical results inaccurate. Spectral identification in these cases established the compounds which were obtained as the desired ones.

As indicated previously, the compounds of the present invention are most unusual in that they can be employed to control the growth of crabgrasses in Southern turfgrasses without appreciably damaging the turfgrasses. Representative tests dealing with this aspect of our invention are described in the following examples.

EXAMPLE VI

In one series of tests demonstrating the efficacy of the compounds of the present invention as crabgrass controls, *Digitaria sanguinalis* seeds were planted in a 3:1 loam-peat mixture and germinated. The plants were grown to the mature stage with periodic application of water and Turf Builder fertilizer.

The chemicals were dissolved in water with Synasol[3] being added as needed to make the compounds go into solution. Tween 20[4] (0.5% by volume) was added to the solution.

[3.] Synasol is a proprietary, denatured ethyl alcohol solvent.
[4.] Tween 20 is one of a series of surface active agents which chemically are polyoxyethylene derivatives of fatty acid partial esters of hexitol anhydrides.

The solutions were applied as sprays at rates providing 5 and 10 pounds of sulfonylurea per acre to 1 X 1 replications. Percent kill was observed and recorded 5 weeks after application. The following results were obtained.

TABLE 2

| Compound | Rate (lbs/acre) | Percent Kill |
|---|---|---|
| 1-(4'-dimethylaminobenzenesulfonyl)-3-ethylurea | 5 | 95 |
|  | 10 | 95 |
| 1-(4'-dimethylaminobenzenesulfonyl)-3-methylurea | 5 | 95 |
|  | 10 | 99 |
| p-dimethylaminobenzenesulfonylurea | 5 | 100 |
|  | 10 | 100 |
| 1-(4'-diethylaminobenzenesulfonyl)-3-ethylurea | 5 | 100 |
|  | 10 | 100 |

EXAMPLE VII

In another series of tests, which demonstrate the tolerance of Southern turfgrasses to our novel sulfonylureas, 1-(4'-dimethylaminobenzenesulfonyl)-3-ethylurea, 1-(4'-dimethylaminobenzenesulfonyl)-3-methylurea, p-diethylaminobenzenesulfonylurea, 1-(4'-diethylaminobenzenesulfonyl)-3-ethylurea, and p-dimethylaminobenzenesulfonylurea were formulated in substantially the same manner as described in Example VI and applied to plots containing stands of mature Floratine St. Augustinegrass, Argentine Bahiagrass, and Tifton 328 Bermudagrass as sprays (3, 6, and 9 pounds per acre) and as a drench (6 pounds per acre). The St. Augustinegrass was free of injury in all plots thirty-two days after application as was the Bermudagrass thirty-four days after application.

Thirty-three days after application the Bahiagrass to which the 1-(4'-diethylaminobenzenesulfonyl)-3-ethylurea was applied was in all cases free of injury as was the Bahiagrass to which 1-(4'-dimethylaminobenzenesulfonyl)-3-ethylurea and p-dimethylaminobenzenesulfonylurea were applied except at the highest rate. At this rate (9 pounds per acre) only minor injury (10%) was noted. The remaining two compounds produced moderate injury at the highest application rate, much less injury at the intermediate rate, and no injury at the low application rate.

EXAMPLE VIII

Our novel compounds can be applied in granular formulations as well as in spray and drench forms as shown by a test in which p-dimethylaminobenzenesulfonylurea was formulated on exfoliated vermiculite in the manner described in U.S. Pat. No. 3,083,089 issued Mar. 26, 1963, to Victor A. Renner for GRANULAR HERBICIDAL COMPOSITION AND METHOD and applied to Tifton 328 Bermudagrass, Bitterblue St. Augustinegrass, and crabgrasses (primarily *Digitaria serotinia*) while the foliage was wet. Thirty-five days after application, final ratings were made.

One hundred percent control of the crabgrasses was obtained at sulfonylurea application rates of 6 and 9 pounds per acre and 88% control (average of two replications) at a 3 pound per acre application rate. There was no visible injury to the St. Augustinegrass. Injury to the Bermudagrass ranged from zero at the 3 pound per acre rate to minor (20%) at the 9 pound per acre rate. The injured Bermudagrass was recovering on this reading date, and there was no evidence of any Bermudagrass kill.

As a check, the same compound was applied in spary form at a rate of 6 pounds per acre. The spray also gave 100% crabgrass control. No observations of turfgrass injury were made.

EXAMPLE IX

In a test conducted in the manner described in Example VI above, seven representative salts of p-dimethylaminobenzenesulfonylurea were applied at rates ranging from 3 to 9 pounds per acre to crabgrass (*Digitaria serotinia*) and to a St. Augustinegrass. Even at the lowest application rate all seven benzenesulfonylurea salts killed 100% of the crabgrass present. At this rate there was no appreciable damage to the St. Augustinegrass as shown by the following tabulated data:

TABLE 3

Rate of Application: 3 Pounds per Acre

| Compound | Percent Kill St. Augustinegrass |
| --- | --- |
| p-dimethylaminobenzenesulfonylurea, potassium salt | 3 |
| p-dimethylaminobenzenesulfonylurea, sodium salt | 3 |
| p-dimethylaminobenzenesulfonylurea, butylammonium salt | 2 |
| p-dimethylaminobenzenesulfonylurea, calcium salt | 5 |
| p-dimethylaminobenzenesulfonylurea, triethylammonium salt | 3 |
| p-dimethylaminobenzenesulfonylurea, diethylammonium salt | 5 |
| p-dimethylaminobenzenesulfonylurea, ammonium salt | 2 |

This data shows that compounds of formula II are highly selective as between crabgrasses and Southern grasses. The data also shows that only low rates of application are necessary; i.e., that these compounds have a high degree of activity on crabgrasses.

EXAMPLE X

In field tests designed to confirm the activity of the sodium salt of p-dimethylaminobenzenesulfonylurea against crabgrasses and the tolerance of St. Augustinegrass to it, the compound was applied in a spray and in a granular formulation prepared as described in Example VIII to replicated plots of Scotts 1081 St. Augustinegrass and to replicated plots of *Digitaria serotinia* in the branching stage. Application rates ranged from 3 to 6 pounds per acre.

Approximately 4 weeks after application, the following averaged observations were made:

TABLE 4

| Type of Formulation | Application Rate (pounds/acre) | % Control, Crabgrass | % Injury St. Augustinegrass |
| --- | --- | --- | --- |
| Granular | 3 | 95 | 7 |
| Granular | 4 | 98 | 12 |
| Granular | 6 | 100 | 20 |
| Liquid | 3 | 87 | 5 |
| Liquid | 4 | 95 | 10 |
| Liquid | 6 | 100 | 25 |

This data shows the selectivity and high degree of control in the field possessed by a representative formula II compound. It again demonstrates that only low application rates are necessary against even mature crabgrass and, in fact, suggests that low rates may be preferable because greater selectivity can be obtained with only a slight sacrifice in the degree of crabgrass control which is obtained.

Compounds closely related to those of the present invention are not suitable for the same purposes. For example, 1-(4'-dimethylaminobenzenesulfonyl)-3-n-butylurea exhibited essentially no post-emergence control of crabgrass in tests of the type described in Example VI (11% kill at an application rate of 5 pounds per acre). 1-(4'-diethylaminobenzenesulfonyl)-3-n-butylurea was tested against six monocots as a preliminary step. It gave no control, even at 5 pounds per acre; and the tests were discontinued. 1-(4'-dimethylaminobenzenesulfonyl)-3-n-hexylurea gave no post-emergence control at a 5 pound per acre application rate.

Compounds such as p-aminobenzenesulfonylurea have preemergence activity on crabgrass (see U.S. Pat. No. 3,637,336 issued Jan. 25, 1972) but are not known to have post-emergence activity against crabgrasses or to be selective between crabgrasses and Southern turfgrasses.

Emphasis has been placed above on the use of the novel compounds disclosed herein as selective, post-emergence crabgrass controls. However, this is by no means the only type of activity displayed by these compounds. For example, at rates of 5 to 25 pounds per acre, representative ones of these controls have been found to give good to complete control of one or more of the following plant varieties: Bluegrass (*Poa pratensis*), *poa annua* (annual bluegrass), pigweed, chicory, clover, barnyardgrass, bermudagrass, wheatgrass, and quackgrass. In some cases they also exhibit growth regulating activity; and p-dimethylaminobenzenesulfonylurea has been shown to have fungicidal activity and to possess activity as a fumigant.

Depending on the particular compound, the type of formulation in which it is incorporated, the characteristics of the particular area to which the formulation is applied, etc., the compounds of the present invention may be applied at single application rates ranging from 1 to 20 or more pounds per acre for the purposes discussed above. For post-emergence crabgrass control, however, it is preferred that they be applied at rates in the range of 5 to 10 pounds per acre. Applications in this range will in most, if not all, cases provide excellent crabgrass control with minimal or no turfgrass injury.

Also, it is within the province of our invention to use repeat applications of the compounds, normally at rates below the single application rates.[5] Repeat applications at low rates will typically provide control of the crabgrass with a minimum of turf injury in even the most difficult circumstances.

As indicated above, the compounds of the present invention can be employed in sprays and drenches and in granular formulations. They may also be combined with a diluent and/or other adjuvants to make a dust and applied with conventional dusting equipment. Depending upon factors such as those discussed above in conjunction with application rates, the proportions of the ingredients in the formulation may vary over a generally wide range. Generally speaking, however, the proportions will fall within the following limits:

TABLE V

| Ingredient | Parts by Weight |
| --- | --- |
| Carrier | 11–15 |
| Solvent-sticking agent | 2–8 |
| Sulfonylurea or salt | 1 |
| Surfactant | 0–0.5 |

5. For example, two applications of 3 pounds per acre of active compound has given excellent results.

Appropriate carriers include organic solvents, water, vermiculite, perlite, diatomaceous earth, clay, ground corn cobs, and other materials such as those described in the *Handbook of Dust Diluents and Carriers* (2d. Ed.), 1955, which is hereby incorporated by reference. For granular formulations, exfoliated vermiculite is preferred.

Diluents, stabilizers, plant nutrients, other pesticides, flow enhancing agents, adhesives, dyes, and other adjuvants may also be used to produce formulations which have other types of activity, which may be safely handled, and which are convenient to apply uniformly and in accurate quantities to the area to be treated. The foregoing and other adjuvants which may be employed are described in *Chemistry of the Pesticides* (3d Ed.), Frear, D. Van Nostrand Company, Inc., New York, N.Y., 1955, and in *Weed Control* (2d Ed.), Robbins et al., McGraw-Hill Book Company, Inc., New York, N.Y., 1952, which are also incorporated by reference herein.

One suitable surfactant (Tween 20) has been identified above. Other suitable surfactants are those listed in *Detergents and Emulsifiers Up-to-Date*, 1968, John W. McCutcheon, Inc., which is also hereby incorporated by reference.

The "solvent" may include or be a sticking agent. Suitable solvents include the one listed above (Synasol) and ethylene and hexylene glycols. Other suitable solvents are described in U.S. Pat. No. 3,076,699 issued Feb. 5, 1963, to Victor A. Renner for GRANULAR HERBICIDAL COMPOSITION AND METHOD and in U.S. Pat. No. 3,083,089.

The Renner patents also disclose methods which may be employed to make granular formulations including the compounds of the present invention. That is, those compounds which are solids at room temperature may be dissolved in an appropriate solvent and adhered to a carrier in the manner disclosed in U.S. Pat. No. 3,083,089. Or particles of the compound may be adhered to a carrier with a suitable sticking agent as described in U.S. Pat. No. 3,076,699.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description; and all changes which come within the meaning and range of equivalency of the claims are therefore intended to be embraced therein.

What is claimed and desired to be secured by Letters Patent is:

1. The method of selectively controlling the growth of undesirable grass in an area in which desirable grass is present, comprisng the step of applying to said area after the emergence of the undesirable grass a herbicidally effective amount of a benzenesulfonylurea of the formula:

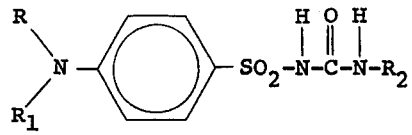

where R is methyl or ethyl, $R_1$ is methyl or ethyl, and $R_2$ is hydrogen, methyl, or ethyl or a salt thereof selected from the group of alkali metal, alkaline earth metal, ammonium, and ammonium substituted with one to three $C_1$–$C_4$ alkyl radicals.

2. A method according to claim 1, wherein the undesirable grass is a *Digitaria spp.*

3. A method according to claim 2, wherein said benzenehydrogorma is applied at a rate of from about 5 to about 10 pounds per acre.

4. A method according to claim 2, wherein the benzenesulfonylurea compound is the sodium salt of a p-dimethylaminobenzenesulfonylurea.

5. The method of selectively controlling the growth of a crabgrass in an area in which desirable grass is present, comprising the step of applying to said area after the emergence of the crabgrass a herbicidally effective amount of a benzenesulfonylurea of the formula:

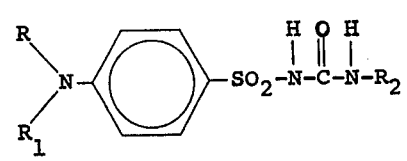

where R is methyl or ethyl, $R_1$ is methyl or ethyl, and $R_2$ is hydrogen, methyl, or ethyl or a salt thereof selected from the group of alkali metal, alkaline earth metal, ammonium, and ammonium substituted with one to three $C_1$–$C_4$ alkyl radicals.

6. A method according to claim 5 in which the desirable grass is a St. Augustine grass.

7. A method according to claim 5 in which the desirable grass is a Bermudagrass.

8. A method according to claim 5 in which the desirable grass is a centipedegrass.

9. A method according to claim 5 in which the desirable grass is a bahiagrass.

10. A method according to claim 5 in which the application of the benzenesulfonylurea to the area is repeated, the rate at which the benzenesulfonylurea is applied being a minimum of 3 pounds per acre in each of the applications.

* * * * *

UNITED STATES PATENT OFFICE
CERTIFICATE OF CORRECTION

PATENT NO. : 3,942,973
DATED : March 9, 1976
INVENTOR(S) : Lawrence S. Wittenbrook et al It is certified that error appears in the above-identified patent and that said Letters Patent are hereby corrected as shown below:

Column 3, line 51, change "compounds can be prepared by following" to --compounds can be prepared by following the method of Kumler with the substituents being added stepwise to the amino nitrogen. That is,--.

Column 3, footnote 2, change "A method of preparing p-diethylaminobenzenesulfonamide is described in Kumler, supra. the method of Kumler with the substituents being added stepwise to the amino nigrogen. That is," to --A method of preparing p-diethylaminobenzenesulfonamide is described in Kumler, supra.--.

Column 7, line 5, change "spary" to --spray--.

Column 10, claim 3, line 2, change "benzenehydrogorma" to --benzenesulfonylurea--.

Signed and Sealed this

Sixth Day of July 1976

[SEAL]

Attest:

RUTH C. MASON
Attesting Officer

C. MARSHALL DANN
Commissioner of Patents and Trademarks